United States Patent [19]

Sandrock et al.

[11] Patent Number: 5,284,872
[45] Date of Patent: Feb. 8, 1994

[54] NITRATO ALKANOIC ACID DERIVATIVES, METHODS FOR THEIR PRODUCTION, PHARMACEUTICAL COMPOSITIONS CONTAINING THE DERIVATIVES AND MEDICINAL USES THEREOF

[75] Inventors: Klaus Sandrock, Langenfeld; Eike Noack, Neuss; Edgar Fritschi, Schwalmtal-Luttelforst; Ralf Kanzler, Leverkusen; Martin Feelisch, Dusseldorf, all of Fed. Rep. of Germany

[73] Assignee: Schwarz Pharma AG, Monheim, Fed. Rep. of Germany

[21] Appl. No.: 681,876

[22] Filed: Apr. 5, 1991

Related U.S. Application Data

[63] Continuation-in-part of Ser. No. 406,165, Sep. 12, 1989, abandoned.

[30] Foreign Application Priority Data

Apr. 10, 1990 [DE] Fed. Rep. of Germany ....... 4011505

[51] Int. Cl.⁵ ................... A61K 31/21; A61K 31/16
[52] U.S. Cl. .................... 514/509; 514/513; 514/625; 558/482; 558/483
[58] Field of Search ............... 514/18, 625, 509, 513; 558/482, 483

[56] References Cited

U.S. PATENT DOCUMENTS 4,900,719 2/1990 Means ................................. 514/18

FOREIGN PATENT DOCUMENTS 861043925 1/1986 European Pat. Off. .
891167009 9/1989 European Pat. Off. .
58-62147A 4/1983 Japan .

OTHER PUBLICATIONS

Lefer et al, Circulation (Sup II) 84:11–620, Abs. No. 2465 Oct. 1991.
Lefer et al. Circulation (Sup II) 84:11–673 Abst No. 2673 Oct. 1991.
Burger, "Medicinal Chemistry" p. 75, 1971.
Campbell Chem Abs. 78(21):136650e & RN38660-08-1, 1973.
JP02091054, Chem. Abs. 113(23):212672x Mar. 30, 1990.
Chemical Abstracts vol. 109, p. 43, (1988), entry 85991r Martin Feelisch et al.
Chemical Abstracts vol. 92, pp. 232 & 233, (1980) entry 176369r, Louis Ignarro et al.
Chemical Abstracts vol. 93, p. 260, (1980) entry 181779z, Louis Ignarro et al.
Chemical Abstracts, vol. 103, pp. 73 and 74 (1985) entry 206021m, H. Schroeder.
Chemical Abstracts, vol. 107, p. 43 (1987) entry 109095p, Martin Feelisch et al.
Campbell et al, J. Org. Chem., vol. 38, No. 6, (1973), pp. 1183–1186.

Primary Examiner—Frederick E. Waddell
Assistant Examiner—Gregory Hook
Attorney, Agent, or Firm—Marshall, O'Toole, Gerstein, Murray & Borun

[57] ABSTRACT

New organic nitrate compounds, formed by condensing a nitrato alkanoic acid with a sulfur-containing amino acid or peptide followed by the reaction of the resulting product with an amino acid, N-acylamino acid, peptide or an N-acyl peptide to produce a thio ester thereof, which prevent nitrate tolerance or overcome existing tolerance and which are useful for the treatment of cardiac diseases including circulatory diseases, coronary dilation, high blood pressure, cardiac insufficiency and for dilating the peripheral vessels.

19 Claims, No Drawings

NITRATO ALKANOIC ACID DERIVATIVES, METHODS FOR THEIR PRODUCTION, PHARMACEUTICAL COMPOSITIONS CONTAINING THE DERIVATIVES AND MEDICINAL USES THEREOF

This application is a continuation-in-part of copending application Ser. No. 07/406,165, filed Sep. 12, 1989 now abandoned.

This invention is concerned with new nitrato alkanoic acid derivatives, methods for their manufacture, pharmaceutical compositions containing the derivatives and uses thereof for medicinal purposes.

BACKGROUND OF THE INVENTION

Organic nitrates (nitric acid esters) have proven effective in the therapy of heart diseases. They exert their effectiveness through cardiac support as well as by alleviating the before and after effects of a load on the heart as well as through improvement of the oxygen supply to the heart by dilation of the coronary vessels.

It has been found in recent years that the organic nitrates which have been previously used in heart therapy, such as glycerol trinitrate (GTN), isosorbid-5-mononitrate or isosorbid dinitrate, because of nitrate tolerance, exhibit a clear drop in efficacy in a relatively short time when continuous high dosages are administered to a patient. Numerous experiments indicate that the presence of sulfhydryl (—SH) groups prevents the development of nitrate tolerance and that an existing tolerance can be reduced by the presence of sulfhydryl groups.

The mechanism by which tolerance is developed is presently understood to involve cysteine. According to the present state of knowledge, the pharmacological action of organic nitrate compounds depends on the presence of cysteine. The organic nitrate forms a common precursor with cysteine. When the precursor decomposes, —NO radicals among others which activate soluble guanylate cyclase, the target enzyme of the smooth muscle cells, are released. Subsequent reactions triggered by the formation of cGMP lead to relaxation or dilation of the vessels.

The reactive and short-lived, and so far, only hypothetical intermediate product would have to be a thioester of nitric acid or a thionitrate. Through intra-molecular rearrangement and other subsequent reactions, which have not yet been established, the final formation of a nitroso thiol is postulated, from which nitrogen monoxide or nitrite ions are liberated. On the other hand, the enzyme-dependent degradation with the aid of GSH reductase would not be of significance for the pharmacological action, because it leads exclusively to the formation of nitrite ions. As already stated, the non-enzymatic degradation needs cysteine and thus it can be exhausted in a dose-dependent manner (exhaustion of the —SH group pool) so that over a long term sufficient —NO, which is the actual activator of guanyl cyclase, can no longer be formed so that the clinical effectiveness is reduced.

In the European patent application 89 116 700.9 specifically synthesized compounds are disclosed which contain nitrato fatty acids (nitrato alkanoic acids) and a group from a sulfur-containing amino acid, for example a peptide. The presence of the sulfhydryl group prevents or resists development of nitrate tolerance and/or a reversal of an existing nitrate tolerance.

Compounds which are disclosed, among others, in the European patent application include those with sulfur-containing amino acids like cysteine or methionine in the form of their methyl, ethyl or propyl esters. Finally, the —SH group present in cysteine can be esterified with a lower alkanoic acid having 2 to 8 carbon atoms.

Although these compounds have already demonstrated valuable pharmacological characteristics with respect to the prevention of nitrate tolerance and/or the reversal of an existing tolerance, they have some disadvantages. Thus, they have low melting points, possess low water solubility, and are difficult to purify.

It is one purpose or object of this invention to provide novel organic compounds, particularly compounds which do not have, or have fewer of, the above-mentioned disadvantages.

DETAILED DESCRIPTION OF THE INVENTION

The stated object is achieved according to the invention by the provision of novel nitrato alkanoic acid derivatives having the general formula (I):

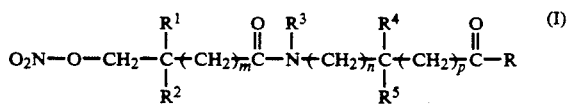

wherein:

R represents hydroxy, a lower alkoxy, a lower alkenoxy, a di-lower alkylamino-lower alkoxy, acylamino-lower alkoxy, acyloxy-lower alkoxy, aryloxy, aryl-lower alkyloxy, substituted aryloxy or substituted aryl-lower alkoxy groups, where the substituent is methyl, halo such as chloro, bromo or fluoro, or methoxy; amino, lower alkylamino, di-lower alkylamino, aryl-lower alkylamino, hydroxy-lower alkylamino and amino acid groups through the peptide bonds, $R^1$ represents hydrogen, an alkyl having 1 to 6 carbon atoms, a substituted lower alkyl in which the substituent is a halo group such as chloro, bromo or fluoro, hydroxy, lower alkoxy, aryloxy, amino, lower alkylamino, acylamino, acyloxy, arylamino, mercapto, lower alkylthio and arylthio, $R^2$ represents the same groups represented in $R^1$, $R^3$ represents hydrogen and lower alkyl, $R^4$ represents hydrogen, lower alkyl, phenyl, methoxy phenyl, phenyl-lower alkyl, methoxyphenyl-lower alkyl, hydroxyphenyl-lower alkyl, hydroxy-lower alkyl, alkoxy-lower alkyl, amino-lower alkyl, acylamino-lower alkyl, mercapto-lower alkyl and lower alkylthio-lower alkyl, $R^5$ represents S-acyl compounds of lower alkylthiol, in particular their amino-acid thio esters, N-acylamino acid thio esters, peptide thio esters, and N-acyl peptide thio esters with 2 to 5 peptide bonded amino acid groups, groups in which R and $R^4$ are bonded with one another by forming an ester or amide, groups in which $R^3$ and $R^4$ are bonded together in the form of an alkylene bridge having 2 to 4 carbon atoms, an alkylene bridge having 2 to 3 carbon atoms and a sulfur atom, an alkylene bridge with 3 to 4 carbon atoms which contains a double bond, or an alkylene bridge as above substituted by hydroxy, lower alkoxy, lower alkyl or di-lower alkyl groups, and m, n and p signify the whole numbers 0 to 10;
as well as physiologically acceptable salts thereof.

More specifically, compounds of formula I are provided in which $R^5$ represents

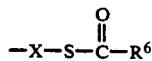

in which X represents a lower alkylene group and particularly —CH$_2$—, —CH$_2$CH$_2$— and

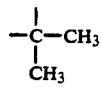

and $R^6$ represents a residue or radical of an amino acid, a derivative of an amino acid, for example an N—, N,O—, or N,S— acylated amino acid and/or ester/amide thereof if a dibasic acid is used from which one carboxylic acid group is needed for esterification with a thiol group, a peptide residue or radical having 2 to 4 peptide bonded amino acid groups or a derivative thereof as described above like N-acyl peptide residue or radical having 2 to 5 peptide bonded amino acid groups.

More specifically, $R^6$ can represent a residue of an amino acid such as glycine, N-acetylglycine, alanine, N-acetylalanine, arginine, N-acetylarginine, N-α-benzoylarginine, cysteine, N-acetylcysteine, N,S-dipivaloylcysteine, cystine, N,N-diacetylcystine, leucine, N-acetylleucine, lysine, N-α-acetyllysine, N ε-acetyllysine, N-αε-diacetyllysine, proline, N-acetylproline, serine, N-acetylserine, O-acetylserine, N,O-diacetylserine, methionine, N-benzoylmethionine, phenylalanine, N-benzoylphenylalanine, N-acetylphenylalanine, asparagine, N-acetylasparagine, N-acetylasparagine monoethyl ester, glutamic acid and N-acetylglutamic acid monomethyl ester.

According to a further feature of the invention, the nitrato alkanoic acid components can have a chain length of C$_2$–C$_6$, they may be straight chain or branched chain, and they may be racemic or optical isomers. Particularly important are the compounds in which $R^1$ and $R^2$ each represent a lower alkyl group, especially those having the same number of carbons, such as groups having 1 to 3 carbons and specifically methyl, ethyl and propyl.

Preferably, the family of nitrato alkanoic acid derivatives of sulfur-containing amino acids of the general formula (I) above contain cysteine or homocysteine as the amino acid.

According to another feature of the invention, the amino acids are present in the stereo-chemical L-form.

The sulfur-containing amino acids can be esterified at the C-terminal end.

Cysteine and/or homocysteine are desirably present as methyl, ethyl or propyl esters.

Particular compounds preferred according to this invention are:

N-nitrato-pivaloyl-S-(N-acetyl-glycyl)-L-cysteine ethyl ester (compound SPM 5186), N-nitrato-pivaloyl-S-(N-acetyl-alanyl)-L-cysteine ethyl ester (compound SPM 5185), and N-nitrato-pivaloyl-S-(N-acetyl-leucyl)-L-cysteine ethyl ester.

Compounds according to the general formula (I) of this invention can be prepared by reacting a compound of the general formula (II)

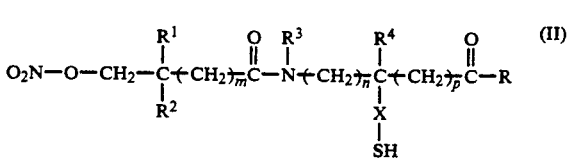

with a compound of the formula

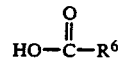

in a thio ester forming reaction to produce a compound of the general formula (IA)

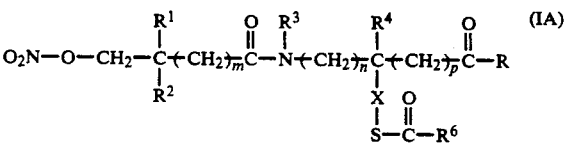

wherein R, $R^1$, $R^2$, $R^3$, $R^4$, m, n, and p have the meaning previously set forth above, X represents a lower alkylene group and particularly —CH$_2$—, —CH$_2$CH$_2$—,

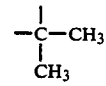

and $R^6$ represents a residue or radical of an amino acid; a derivative of an amino acid for example an N—; N,O—; or N,S— acylated amino acid and/or ester/amide thereof if a dibasic acid is used from which one carboxylic acid group is needed for esterification with a thiol group, a peptide residue or radical having 2 to 4 peptide bonded amino acid groups or a derivative thereof as described above like an N-acyl peptide residue or radical having 2 to 5 peptide bonded amino acid groups.

Representative amino acids which can be used in the process are glycine, N-acetylglycine, alanine, N-acetylalanine, arginine, N-acetylarginine, N-α-benzoylarginine, cysteine, N-acetylcysteine, N,S-dipivaloylcysteine, cystine, N,N-diacetylcystine, leucine, N-acetylleucine, lysine, N-α-acetyllysine, N ε-acetyllysine, N-αε-diacetyllysine, proline, N-acetylproline, serine, N-acetylserine, O-acetylserine, N,O-diacetylserine, methionine, N-benzoylmethionine, phenylalanine, N-benzoylphenylalanine, N-acetylphenylalanine, asparagine, N-acetylasparagine, N-acetylasparagine monoethyl ester, glutamic acid and N-acetylglutamic acid monomethyl ester.

The preparation of the starting compounds, used in the subject invention and which are within general formula (II), is readily effected by procedures disclosed in EPA 89 116 700.9 and in the copending Sandrock et al U.S. patent application Ser. No. 07/406,165, filed Sep. 12, 1989, the entire contents of which is incorporated herein by reference and which was refiled as continuation-in-part application Ser. No. 07/818,502 filed Jan. 8, 1992. Thus, nitrato alkanoic acids of the general formula (A)

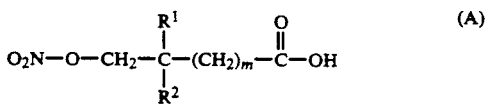

(A)

in which $R^1$, $R^2$ and m have the meaning previously set forth herein, which can be reacted in the form of the free acid, a reactive acylhalide, acid azide, ester, and acid anhydrides, is reacted with a compound of the general formula (B)

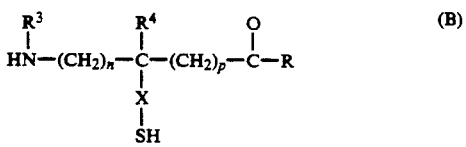

(B)

wherein R, $R^3$, $R^4$, X, n and p have the meaning previously set forth above, containing amino acids and/or peptides thereby forming compounds of the general formula (II).

Reactive derivatives of the nitrato alkanoic acids which can be used in the process are, for example, acid halides, acid anhydrides, activated amides and activated esters. Preferably, acid chlorides, acid azides, symmetrical acid anhydrides; activated esters and mixed anhydrides with organic or inorganic acids can be used.

The condensation reaction of a nitrato alkanoic acid with an amino group of an amino acid can also be carried out in an inert solvent and in the presence of a condensing agent which promotes the formation of an acid amide bond, a carbodiimide such as N,N'-dicyclohexyl carbodiimide or a similar carbodiimide, an imine compound such as diphenylketene-N-cyclohexylimine or pentamethyleneketene-N-cyclohexylimine, or a phosphate or phosphite such as triethyl phosphite, ethyl polyphosphate or isopropyl polyphosphate, over a period of 1–48 hours at temperatures from $-10°$ C. to the refluxing temperature of the solvent used.

The compounds of the general formulas (I) and (IA) can be converted into their pharmacologically safe acid addition salts by adding the compounds to an organic, or aqueous organic, solvent with an equivalent amount of a suitable inorganic or organic acid. Suitable acids are hydrochloric acid, hydrobromic acid, nitric acid, phosphoric acid, sulfuric acid, formic acid, acetic acid, propionic acid, oxaluric acid, fumaric acid, maleic acid, succinic acid, adipic acid, benzoic acid, salicylic acid, O-acetoxygenzoic acid, cinnamic acid, naphthoic acid, mandelic acid, citric acid, malic acid, tartaric acid, aspartic acid, glutamic acid, methane-sulphonic acid and toluene-p-sulphonic acid.

The novel compounds according to this invention of the general formulas (I) and (IA) and their salts can be administered orally, intravenously or parenterally to a patient as a pharmaceutical preparation in liquid or solid form. The preferred liquid carrier is water, which can contain additives common in injectable solutions, such as stabilizers, solubilizers and buffers. Some suitable additives are, for example, tartrate and citrate buffers, ethanol, complexing agents like ethylenediaminetetraacetic acid and their non-toxic salts, high molecular weight liquid polymers, such as liquid polyethylene oxide, for viscosity control. Solid carrier substances which can be used are, for example, starch, lactose, mannitol, methyl cellulose, talcum, highly dispersed gelatinous silicic acid, higher molecular weight fatty acids such as stearic acid, gelatin, agar-agar, calcium phosphate, magnesium stearate, animal and vegetable fats and solid high molecular weight polymers as, for example, polyethylene glycols. Preparations suitable for oral application may contain, if desired, flavoring substances and sweeteners.

According to another aspect of this invention, the drugs or pharmaceutical preparations can contain a specific amount of one or more of the compounds according to formulas (I) and (IA). Pharmaceutical compositions can contain about 1 to 300 mg of active compound per unit dosage form, such as a tablet or capsule. A liquid pharmaceutical composition can contain about 5 to 200 mg of active compound per liter.

The compounds of formulas (I) and (IA) can be used for the treatment of circulatory diseases, for example, for coronary dilation, as means for the treatment of high blood pressure, heart insufficiency, and for the dilation of the peripheral vessels, including vessels in the brain and kidney.

Pharmaceutical preparations containing a predetermined amount of one or several of the compounds according to this invention can be administered once daily in the form of slow or delayed release preparations, or several times a day at regular intervals, such as 2 to 3 times daily. About 5 to 300 mg, and desirably 20 to 300 mg, based on a patient body weight of 75 kg., of one or a combination of the effective agents can be administered per day to a patient. The compounds according to this invention can be administered in the form of injections 1 to 8 times daily or by means of an intravenous drip. Normally, an administration of about 5 to 200 mg/day are sufficient.

A typical tablet can have the composition:

| | | |
|---|---|---|
| 1) | N-nitrato-pivaloyl-S-(N-acetyl-glycyl)-L-cysteine ethyl ester | 25 mg |
| 2) | Starch, U.S.P. | 57 mg |
| 3) | Lactose, U.S.P. | 73 mg |
| 4) | Talcum, U.S.P. | 9 mg |
| 5) | Stearic acid | 6 mg |

The substances 1, 2 and 3 are sifted, granulated, homogeneously mixed with 4 and 5, and finally tableted.

The following examples are presented to further illustrate the invention.

EXAMPLE 1

Preparation of N-nitrato-pivaloyl-S-(N-acetyl-glycyl)-L-cysteine ethyl ester (Compound SPM 5186)

Forty-eight g (0.41 mole) of N-acetyl-glycine was suspended with stirring at room temperature in 300 ml of methylene chloride ($CH_2Cl_2$) and then cooled to 10° C. A solution of 109.8 g (0.373 mole) of N-nitrato-pivaloyl-L-cysteine ethyl ester in 300 ml of $CH_2Cl_2$ was added while stirring during a weak exothermic reaction. The reaction mixture was cooled to 5° C. while stirring and a solution of 84.6 g (0.41 mole) of di-cyclohexyl carbodiimide (DDC) was slowly added drop-by-drop in 200 ml of $CH_2Cl_2$ while stirring so that the temperature was in a range between 5° C. and 10° C. After heating to room temperature, the mixture was stirred for four days at room temperature. The solid DDC urea was withdrawn and washed twice with 100 ml aliquots of $CH_2Cl_2$.

The combined $CH_2Cl_2$ aliquots was washed once with 200 ml of a solution containing 9% $NaHCO_2$, 300 ml of 1 N HCl, and 300 ml of distilled water. Finally, the methylene chloride phase was dried via water-free sodium sulphate and evaporated on a rotatory evaporator (Rotavapor ®, Buechi) until a constant weight was obtained.

The yield amounted to 162.9 g (theoretical 146.74 g) of N-nitrato-pivaloyl-S-(N-acetyl-glycyl)-L-cysteine ethyl ester as a light yellow oil.

162.9 g of N-nitrato-pivaloyl-S-(N-acetylglycyl)-L-cysteine ethyl ester was dissolved in 470 ml of ethyl acetate at room temperature. After stirring for 15 minutes at room temperature, the undissolved white sediment was filtered out. The clear light yellow filtrate was mixed with 390 ml of n-hexane by stirring slowly at room temperature.

Seed crystals were added to the solution and the solution was stirred overnight at room temperature. The settled crystals were withdrawn and washed twice with separate 100 ml aliquots of a mixture of 20 ml of ethyl acetate and 80 ml of n-hexane at room temperature.

The crystals were dried in a vacuum drying oven at room temperature, vacuum 2 Torr, until a constant weight was obtained.

The yield amounted to 85.4 g (theoretical 146.74 g) of N-nitrato-pivaloyl-S-(N-acetyl-glycyl)-L-cysteine ethyl ester. M.P. 71.8° C.

EXAMPLE 2

Preparation of N-nitrato pivaloyl S (N-acetyl-alanyl)-L-cysteine ethyl ester (Compound SPM 5185)

53.8 g (0.41 mole) of N-acetyl-alanine was suspended in 300 ml of methylene chloride ($CH_2Cl_2$) while stirring at room temperature and then cooled to 10° C. A solution of 109.8 g (0.373 mole) of N-nitrato-pivaloyl-L-cysteine ethyl ester in 300 ml of $CH_2Cl_2$ was then added while stirring and a weak exothermic reaction took place. The reaction mixture was cooled to 5° C. while stirring, and a solution of 84.6 g (0.41 mole) of dicyclohexyl carbodiimide (DDC) in 200 ml of $CH_2Cl_2$ was slowly added drop-by-drop, while stirring, so that the temperature was in the range of 5° C. and 10° C. After the mixture had been warmed to room temperature, it was stirred for four days at room temperature. Solid DDC urea was withdrawn and washed twice with separate 100 ml aliquots of $CH_2Cl_2$.

The combined methylene chloride phases was consecutively washed twice with separate 200 ml aliquots of a solution containing 9% $NaHCO_3$, 300 ml of N HCl and 300 ml of distilled water. Finally, the methylene chloride phase was dried via water-free sodium sulphate and evaporated on a rotary evaporator (Rotavapor ®, Buechi) until a constant weight was obtained.

The yield amounted to 160.5 g (theoretical 151.84 g) of N-nitrato-pivaloyl-S-(N-acetyl-alanyl)-L-cysteine ethyl ester as a light yellow oil.

160.5 g of N-nitrato-pivaloyl-S-(N-acetyl-alanyl)-L-cysteine ethyl ester was dissolved in 345 ml of ethyl acetate at room temperature. After stirring for 15 minutes at room temperature, an undissolved white sediment was filtered off. The clear, light yellow filtrate was mixed at room temperature while stirring slowly with 345 ml of n-hexane.

Seed crystals were added to this solution and stirred at room temperature over night. The settled crystals were withdrawn and washed twice with separate 100 ml aliquots of a mixture of 20 ml of ethyl acetate and 80 ml of n-hexane at room temperature.

The crystals were dried in a vacuum drying oven at room temperature, vacuum 2 Torr, until the weight was constant.

The yield amounted to 78.2 g (thoretical 151.84 g) of N-nitrato-pivaloyl-S-(N-acetyl-alanyl)-L-cysteine ethyl ester. MP: 76.6° C.

EXAMPLE 3

Preparation of N-nitrato-pivaloyl-S-(N-acetylleucyl)-L-cysteine ethyl ester

Six g. (0.02 mole) of N-nitrato-pivaloyl-L-cysteine ethyl ester is dissolved in 100 ml of dichloromethane. At 10° C. and under a nitrogen atmosphere 5.19 g (0.03 mole) of N-acetyl leucine and 0.1 g of dimethylamino pyridine (DMAP) is slowly added. Then 6.15 g (0.03 mole) of dicyclohexyl carbodiimide (DCC) dissolved in 80 ml of dichloromethane is added drop-by-drop. This mixture is stirred over night at room temperature.

The precipitate is then removed. The residual solution is consecutively extracted with equal amounts of 0.1 N HCl solution, saturated $NaHCO_3$ solution and distilled $H_2O$. Then residual solvent is withdrawn by use of a rotary evaporator (Rotavapor ®, Buechi) leaving 10 g of an oily residue.

The 10 g of oily substance is dissolved in 45 ml of ethanol and 40 ml of $H_2O$ which is slightly warmed. The product is crystallized out overnight in a refrigerator. The crystals are withdrawn and dried in a vacuum drying oven. The product structure is confirmed by mass spectrography. Melting point: 91.4° C. HPLC Analysis=98.7%; Yield: 5g=0.012 mole=57.4% of theoretical.

Apart from the inventive objective to improve water solubility, glycine and alanine are the preferred SH—protecting groups.

Both of these amino acids are endogenous compounds with a well known and nontoxic metabolism. An increase in plasma concentration of either of these amino acids as a result of drug metabolism will have no harmful effect as their basal plasma concentration in humans is usually in the high $\mu$molar range (344±29 and 215±8 $\mu$mol/l for alanine and glycine, respectively (Am.J.Clin.Nutr., 1970,23:986)).

The increased hydrophilicity of amino acid-containing nitrate compounds was expected to result in an accelerated membrane permeation. Together with a weaker strength of the thioester bond this was thought to enhance its vasodilator potency by increasing bioconversion to NO after deesterification in the vascular target cell.

The following preliminary pharmacological data obtained with compound SPM 5185 (Example 2) and compound SPM 5186 (Example 1) underline the advantages of the above described approach.

All organic nitrates react non-enzymatically with the SH— group-containing amino acid cysteine to form nitratopivaline carboxylic acid-L-cysteine ethyl ester (SPM 3672), the proposed active component of compounds SPM 5185 and SPM 5186, which was found to release NO spontaneously even in the absence of exogenous cysteine due to the presence of its free thiol group (42.7±9.8 nM NO/min at pH 7.4 and a concentration of 1 mM). The rate of NO formation from 1 mM of compounds SPM 5185 and SPM 5186 was in the range of that obtained with ISDN (isosorbid dinitrate) under the same conditions, SPM 5185 being slightly more potent than SPM 5186 (35.1±5.1 and 24.8±5.4 nM NO/min at pH 7.4). In accordance with these data compound SPM 3672 stimulated soluble guanylate cyclase in the absence of exogenous cysteine and the addition of cysteine did not further enhance enzyme stimulation. Due to their pro-drug character, SPM 5185 and SPM 5186 stimulated guanylate cyclase only in the presence of cysteine.

Compounds SPM 5185 and SPM 5186 caused a similar concentration-dependent relaxation of precontracted rat aortic rings with a potency exceeding that of ISDN (isosorbid dinitrate) by a factor of 5 (EC$_{50}$ approx. $10^{-6}$ M).

The effect of a single peroral application of SPM 5186 on endothelium dependent and independent blood pressure regulation was investigated in chronically instrumented conscious rats with acetylcholine and adenosine serving as test stimuli. Neither in normotonous (WKY) nor in spontaneously hypertensive rats (SHR) could any significant alteration of endogenous dilator mechanisms be observed after single oral application of compound SPM 5186.

Peroral application of compound SPM 5185 to normotonous conscious rats had nearly no influence on mean arterial pressure and caused only a slight increase in heart rate. In spontaneously hypertensive rats the same dose of SPM 5186 caused a marked decrease of both systolic and diastolic arterial blood pressure, indicating enhancement of arterial compliance and reduction of total peripheral resistance.

The hemodynamic profile of SPM 5185 and SPM 5186 in direct comparison to classical nitrates was investigated in conscious beagle dogs. Peroral as well as intravenous application of SPM 5185 and SPM 5186 (dose range: 0.01–1 μmol/kg i.v. and 1–10 μmol/kg p.o., respectively) lead to a dose-dependent decrease in mean arterial and venous pressure with predominant action on capacitance vessels. Arterial vessel compliance was enhanced whereas cardiac output remained unaffected. Estimated duration of action characterized both compounds as long-acting nitrates. Construed dose-response curves for SPM 5185, SPM 5186, GTN (glycerol trinitrate) and IS-5-N (isosorbid-5-mononitrate) clearly demonstrate that both new nitrates are even more effective than the most potent classical nitrate GTN in reducing arterial and central venous pressure in vivo.

The structural relationship of the three compounds whose pharmacological properties are summarized above will be readily seen by reference to the following formulas:

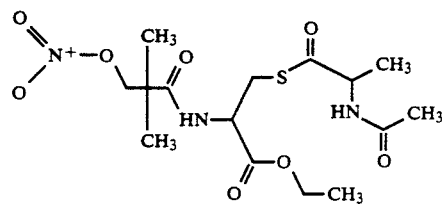

SPM 5185

-continued
N-Piv-CyEt-S-N-Ac-Ala

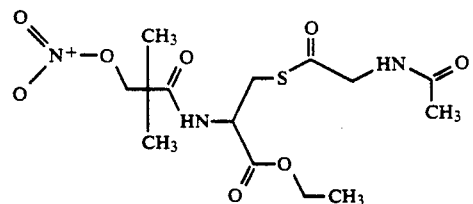

SPM 5186
N-Piv-CyEt-S-N-Ac-Gly

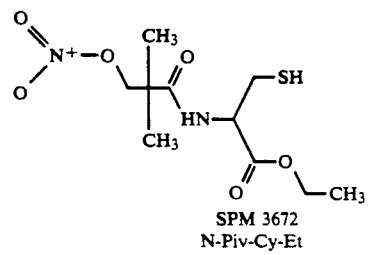

SPM 3672
N-Piv-Cy-Et

What is claimed is:
1. A compound of the formula

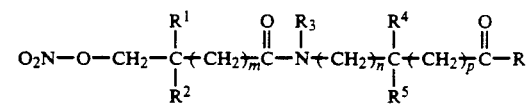

wherein:
R is hydroxy or lower alkoxy,
R$^1$ is hydrogen or lower alkyl,
R$^2$ is hydrogen or lower alkyl,
R$^3$ is hydrogen or lower alkyl,
R$^4$ is hydrogen or lower alkyl
R$^5$ represents

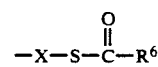

wherein X represents a lower alkylene group and particularly —CH$_2$—, —CH$_2$CH$_2$— or

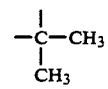

R$^6$ represents a residue or radical of an amino acid selected from the group consisting of glycine, N-acetylglycine, alanine, N-acetylalanine, arginine, N-acetylarginine, N-α-benzoylarginine, cysteine, N-acetylcysteine, N,S-dipivaloylcysteine, cystine, N,N-diacetylcystine, leucine, N-acetylleucine, lysine, N-α-acetyllysine, N-ε-acetyllysine, N-αε-diacetyllysine, proline, N-acetylproline, serine, N-acetylserine, O-acetylserine, N,O-diacetylserine, methionine, N-benzoylmethionine, phenylalanine, N-benzoylphenylalanine, N-acetylphenylalanine, asparagine, N-acetylasparagine, N-acetylasparagine monoethyl ester, glutamic acid and N-acetylglutamic acid monomethyl ester; and
m, n, and p represent 0 to 1.

2. A compound according to claim 1 in which $R^1$ is hydrogen and $R^2$ is a lower alkyl having 1 to 4 carbon atoms.

3. A compound according to claim 1 in which $R^1$ is a lower alkyl having 1 to 3 carbon atoms and $R^2$ is a lower alkyl having 1 to 3 carbon atoms.

4. A compound according to claim 1 in the form of optical isomers.

5. A compound according to claim 1 in the form of racemic mixtures.

6. A compound according to claim 1 in the stereochemical L-form.

7. A compound according to claim 1 in the form of acid addition salts.

8. A compound according to claim 1 in which the alkoxy groups represented by R are methoxy, ethoxy and propoxy.

9. A N-nitrato-pivaloyl-S-(N-acetyl-glycyl)-L-cysteine ester.

10. A N-nitrato-pivaloyl-S-(N-acetyl-alanyl)-L-cysteine ester.

11. A N-nitrato-pivaloyl-S-(N-acetyl-leucyl)-L-cysteine ester.

12. A pharmaceutical composition containing as an active ingredient an effective amount of a compound having the formula

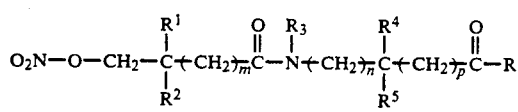

wherein:
R is hydroxy or lower alkoxy,
$R^1$ is hydrogen or lower alkyl,
$R^2$ is hydrogen or lower alkyl,
$R^3$ is hydrogen or lower alkyl,
$R^4$ is hydrogen or lower alkyl
$R^5$ represents

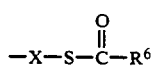

wherein X represents a lower alkylene group and particularly —CH$_2$—, —CH$_2$CH$_2$— or

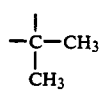

$R^6$ represents a residue or radical of an amino acid selected from the group consisting of glycine, N-acetylglycine, alanine, N-acetylalanine, arginine, N-acetylarginine, N-α-benzoylarginine, cysteine, N-acetylcysteine, N,S-dipivaloylcysteine, cystine, N,N-diacetylcystine, leucine, N-acetylleucine, lysine, N-α-acetyllysine, N-ε-acetyllysine, N-αε-diacetyllysine, proline, N-acetylproline, serine, N-acetylserine, O-acetylserine, N,O-diacetylserine, methionine, N-benzoylmethionine, phenylalanine, N-benzoylphenylalanine, N-acetylphenylalanine, asparagine, N-acetylasparagine, N-acetylasparagine monoethyl ester, glutamic acid and N-acetyl-glutamic acid monomethyl ester; and
m, n, and p represent 0 to 1; and
a nontoxic pharmaceutical carrier.

13. A pharmaceutical composition according to claim 12 in unit dosage form comprising a compound selected from the group consisting of:
  a N-nitrato-pivaloyl-S-(N-acetyl-glycyl)-L-cysteine ester,
  a N-nitrato-pivaloyl-S-(N-acetyl-alanyl)-L-cysteine ester, and
  a N-nitrato-pivaloyl-S-(N-acetyl-leucyl)-L-cysteine ester.

14. A pharmaceutical composition according to claim 12 in which the pharmaceutical carrier is a liquid and the pharmaceutical composition contains about 5 to 200 mg of active compound per liter.

15. A pharmaceutical composition according to claim 12 in unit dosage form in which the pharmaceutical carrier is a solid and the pharmaceutical composition contains about 5 to 300 mg of active compound per unit dosage form.

16. A method of treating a patient to effect a member of the group consisting of treating angina pectoris, effecting coronary dilation, reducing blood pressure, treating heart insufficiency, dilating peripheral vessels, enhancing arterial compliance and reducing total peripheral resistance, comprising administering to a patient, in need of such treatment, a pharmaceutical composition containing as an active ingredient, an effective amount of a compound having the formula

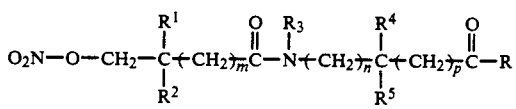

wherein:
R is hydroxy or lower alkoxy,
$R^1$ is hydrogen or lower alkyl,
$R^2$ is hydrogen or lower alkyl,
$R^3$ is hydrogen or lower alkyl,
$R^4$ is hydrogen or lower alkyl
$R^5$ represents

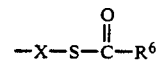

wherein X represents a lower alkylene group and particularly —CH$_2$—, —CH$_2$CH$_2$— or

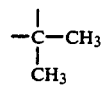

$R^6$ represents a residue or radical of an amino acid selected from the group consisting of glycine, N-acetylglycine, alanine, N-acetylalanine, arginine, N-acetylarginine, N-α-benzoylarginine, cysteine, N-acetylcysteine, N,S-dipivaloylcysteine, cystine, N,N-diacetylcystine, leucine, N-acetylleucine, lysine, N-α-acetyllysine, N-ε-acetyllysine, N-αε-diacetyllysine, proline, N-acetylproline, serine, N-acetylserine, O-acetylserine, N,O-diacetylserine, methionine, N-benzoylmethionine, phenylalanine, N-benzoylphenylalanine, N-acetylphenylalanine, asparagine, N-acetylasparagine, N-acetylasparagine monoethyl ester, glutamic acid and N-acetyl-glutamic acid monomethyl ester; and m, n, and p represent 0 to 1; and a nontoxic pharmaceutical carrier.

17. A method according to claim 16 in which the pharmaceutical carrier is a liquid and the pharmaceutical composition contains about 5 to 200 mg of active compound per liter.

18. A method according to claim 16 in which the pharmaceutical composition is in unit dosage form, the pharmaceutical carrier is a solid and the pharmaceutical composition contains about 1 to 300 mg of active compound per unit dosage form.

19. A method according to claim 16 in which the compound is selected from the group consisting of:
- a N-nitrato-pivaloyl-S-(N-acetyl-glycyl)-L-cysteine ester,
- a N-nitrato-pivaloyl-S-(N-acetyl-alanyl)-L-cysteine ester, and
- a N-nitrato-pivaloyl-S-(N-acetyl-leucyl)-L-cysteine ester.

* * * * *